United States Patent
Levinson et al.

(10) Patent No.: US 8,285,390 B2
(45) Date of Patent: Oct. 9, 2012

(54) MONITORING THE COOLING OF SUBCUTANEOUS LIPID-RICH CELLS, SUCH AS THE COOLING OF ADIPOSE TISSUE

(75) Inventors: Mitchell E. Levinson, Pleasanton, CA (US); Jesse N. Rosen, Albany, CA (US); Corydon A. Hinton, Oakland, CA (US); Kevin S. Springer, Livermore, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 47 days.

(21) Appl. No.: 12/196,246

(22) Filed: Aug. 21, 2008

(65) Prior Publication Data

US 2009/0149929 A1 Jun. 11, 2009

Related U.S. Application Data

(60) Provisional application No. 60/957,130, filed on Aug. 21, 2007.

(51) Int. Cl.
*A61F 7/00* (2006.01)
(52) U.S. Cl. .......................................... 607/99; 607/96
(58) Field of Classification Search ............. 607/99, 607/113
See application file for complete search history.

(56) References Cited

U.S. PATENT DOCUMENTS

| | | |
|---|---|---|
| 681,806 A | 9/1901 | Mignault |
| 889,810 A | 6/1908 | Robinson |
| 2,516,491 A | 7/1950 | Swastek |
| 2,766,619 A | 10/1956 | Tribus et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |

(Continued)

FOREIGN PATENT DOCUMENTS

CN 1511503 7/2004

(Continued)

OTHER PUBLICATIONS

U.S. Appl. No. 12/275,002, filed Nov. 20, 2008, Martens.

(Continued)

*Primary Examiner* — Roy Gibson
*Assistant Examiner* — Kaitlyn Smith
(74) *Attorney, Agent, or Firm* — Perkins Coie LLP

(57) ABSTRACT

A system and method of monitoring, controlling and/or detecting events during the removal of heat from subcutaneous lipid-rich tissue is described. In some examples, the system detects an increase in temperature at a treatment device in contact with the skin of a subject, determines that the increase in temperature is related to a treatment event, and performs an action based on the determination. In some examples, the system shuts off the treatment device, alerts an operator, or reduces the cooling in response to a determined treatment event.

6 Claims, 9 Drawing Sheets

U.S. PATENT DOCUMENTS

| | | |
|---|---|---|
| 4,002,221 A | 1/1977 | Buchalter |
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,505,726 A | 4/1996 | Meserol |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Goncalves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,049,927 A | 4/2000 | Thomas et al. |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,548,297 B1 | 4/2003 | Kuri-Harcuch et al. |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,699,266 B2 | 3/2004 | Lachenbruch et al. |
| 6,718,785 B2 | 4/2004 | Bieberich |
| 6,741,895 B1 | 5/2004 | Gafni et al. |
| 6,746,474 B2 | 6/2004 | Saadat |

| | | |
|---|---|---|
| 6,749,624 B2 | 6/2004 | Knowlton |
| 6,764,502 B2 | 7/2004 | Bieberich |
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,022,121 B2 | 4/2006 | Stern et al. |
| 7,037,326 B2 | 5/2006 | Lee et al. |
| 7,077,858 B2 | 7/2006 | Fletcher et al. |
| 7,081,111 B2 | 7/2006 | Svaasand et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,367,341 B2 | 5/2008 | Anderson et al. |
| 7,713,266 B2 | 5/2010 | Elkins et al. |
| 7,854,754 B2 | 12/2010 | Ting et al. |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0103520 A1 | 8/2002 | Latham |
| 2002/0117293 A1 | 8/2002 | Campbell |
| 2002/0120315 A1 | 8/2002 | Furuno et al. |
| 2002/0151887 A1 | 10/2002 | Stern et al. |
| 2002/0188286 A1 | 12/2002 | Quijano et al. |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0199226 A1 | 10/2003 | Sommer et al. |
| 2003/0220674 A1 | 11/2003 | Anderson et al. |
| 2003/0236487 A1 | 12/2003 | Knowlton |
| 2004/0006328 A1 | 1/2004 | Anderson |
| 2004/0009936 A1 | 1/2004 | Tang et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1* | 4/2004 | Altshuler et al. ............. 600/1 |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0199226 A1 | 10/2004 | Shadduck |
| 2004/0210214 A1 | 10/2004 | Knowlton |
| 2004/0210287 A1 | 10/2004 | Greene |
| 2004/0259855 A1 | 12/2004 | Anderson et al. |
| 2005/0049661 A1 | 3/2005 | Koffroth |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1* | 11/2005 | Anderson et al. ............. 606/20 |
| 2006/0030778 A1 | 2/2006 | Mendlein et al. |
| 2006/0036300 A1 | 2/2006 | Kreindel |
| 2006/0074313 A1 | 4/2006 | Slayton et al. |
| 2006/0079852 A1 | 4/2006 | Bubb et al. |
| 2006/0122509 A1 | 6/2006 | Desilets |
| 2006/0200063 A1 | 9/2006 | Munro et al. |
| 2006/0234899 A1 | 10/2006 | Nekmard et al. |
| 2006/0270745 A1 | 11/2006 | Hunt et al. |
| 2006/0293734 A1 | 12/2006 | Scott et al. |
| 2007/0010861 A1 | 1/2007 | Anderson et al. |
| 2007/0032561 A1 | 2/2007 | Lin et al. |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0255362 A1 | 11/2007 | Levinson et al. |
| 2007/0270925 A1 | 11/2007 | Levinson |
| 2007/0282249 A1 | 12/2007 | Quisenberry et al. |
| 2008/0046047 A1 | 2/2008 | Jacobs |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0140371 A1 | 6/2008 | Warner |
| 2008/0183164 A1 | 7/2008 | Elkins et al. |
| 2008/0287839 A1* | 11/2008 | Rosen et al. .................... 601/18 |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2010/0081971 A1* | 4/2010 | Allison .......................... 601/2 |
| 2010/0280582 A1 | 11/2010 | Baker et al. |
| 2011/0077723 A1 | 3/2011 | Parish et al. |
| 2012/0022518 A1 | 1/2012 | Levinson |

FOREIGN PATENT DOCUMENTS

| | | |
|---|---|---|
| CN | 1741777 A | 3/2006 |
| CN | 1817990 A | 8/2006 |
| DE | 532976 C | 9/1931 |
| DE | 2851602 | 6/1980 |
| DE | 4213584 A1 | 11/1992 |
| DE | 4224595 | 1/1994 |
| EP | 0263069 A2 | 4/1988 |
| EP | 0397043 | 11/1990 |
| EP | 0406244 A1 | 1/1991 |
| EP | 0598824 A1 | 6/1994 |
| GB | 2286660 A | 8/1995 |
| GB | 2323659 A | 9/1998 |
| JP | 63076895 A | 4/1988 |
| JP | 03051964 A | 3/1991 |
| JP | 3259975 A | 11/1991 |
| JP | 4093597 A | 3/1992 |
| JP | 6282977 A | 10/1994 |
| JP | 7268274 A | 10/1995 |
| JP | 09164163 A | 6/1997 |
| JP | 10216169 A | 8/1998 |
| JP | 3065657 | 11/1999 |
| JP | 2000503154 A | 3/2000 |
| JP | 2002543668 A | 12/2002 |
| JP | 2004013600 A | 1/2004 |
| JP | 2004073812 | 11/2004 |
| JP | 2005039790 A | 2/2005 |
| JP | 3655820 | 3/2005 |
| JP | 200565984 | 3/2005 |
| JP | 2005110755 | 4/2005 |
| JP | 2005520608 T | 7/2005 |
| JP | 2005323716 | 11/2005 |
| JP | 2006026001 A | 2/2006 |
| JP | 2006520949 A | 9/2006 |
| JP | 2008532591 | 8/2008 |
| KR | 1020040094508 | 11/2004 |
| SU | 532976 | 11/1978 |
| TW | 0476644 | 2/2002 |
| WO | WO 1985003216 | 8/1985 |
| WO | WO-9636293 A1 | 11/1996 |
| WO | WO-9637158 A1 | 11/1996 |
| WO | WO-9705828 A1 | 2/1997 |
| WO | WO-9722262 A2 | 6/1997 |
| WO | WO-9841156 A1 | 9/1998 |

| | | | |
|---|---|---|---|
| WO | WO-9841157 A1 | 9/1998 |
| WO | WO-9938469 A1 | 8/1999 |
| WO | WO-0044346 A1 | 8/2000 |
| WO | WO0067685 | 11/2000 |
| WO | WO0114012 | 3/2001 |
| WO | WO-0205736 A2 | 1/2002 |
| WO | WO-02102921 A1 | 12/2002 |
| WO | WO-03078596 A2 | 9/2003 |
| WO | WO-04000098 A2 | 12/2003 |
| WO | WO-2004080279 A2 | 9/2004 |
| WO | WO-2005046540 A1 | 5/2005 |
| WO | WO-2006066226 A1 | 6/2006 |
| WO | WO2006094348 | 9/2006 |
| WO | WO-2006127467 A2 | 11/2006 |
| WO | WO-2007041642 A2 | 4/2007 |
| WO | WO-2010127315 A2 | 11/2010 |
| WO | WO-2012012296 A1 | 1/2012 |

OTHER PUBLICATIONS

U.S. Appl. No. 12/275,014, filed Nov. 20, 2008, Martens.
U.S. Appl. No. 12/337,544, filed Dec. 17, 2008, Alison.
Ardevol, "Cooling rates of tissue samples during freezing with liquid nitrogen," J. of Biochem and Biophysical Methods, 27, 77-86 (1993).
Bohm et al., "Saline-enhanced radiofrequency ablation of breat tissue: an in vitro feasibility study," Invest Radiol, 2000, pp. 149-157, vol. 35—issue (3).
Bondei, E. et al., "Disorders of Subcutaneous Tissue (Cold Panniculitis)," Dermatology in General Medicine, Chapter 108, Section 16: 1333-1334, 1993.
Burge, S.M. et al., "Hair Follicle Destruction and Regeneration in Guinea Pig Skin after Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.
Epstein, E.H. et al., "Popsicle Panniculitis," The New England Journal of Medicine, 282(17):996-67, 1970.
Gage, "Current Progress in Cryosurgery," Cryobiology 25, 483-486 (1988).
Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2007/062508; Applicant: Juniper Medical, Inc.; Date of Mailing: Jul. 20, 2007, 13 pages.
International Search Report for EP07758558.6; Applicant: Zeltiq Aesthetics, Inc.; Mailed on Jul. 20, 2007, 4 pages.
International Search Report for PCT/US2005/045988; (Apr. 25, 2006).
Kellum, R.E. et al., "Sclerema Neonatorum: Report of Case and Analysis of Subcutaneous and Epidermal-Dermal Lipids by Chromatographic Methods," Arch. Derm., 97:372-80, 1968.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Moschella, S.L. et al., "Diseases of the Subcutaneous Tissue," Derm., Section 2:1169-1181, 1985.
Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis-a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 11/435,502; Date of Mailing: Jul. 17, 2009, 10 pages.

Pease, "An Integrated Probe for Magnetic Resonance Imaging Monitored Skin Cryosurgery," Journal of Biomedical Engineering 117, 59-63, (1995).

Pech, "Attenuation values, volume changes and artifacts in tissue due to freezing," Acta Radiologica 6, 779-782 (1987).

Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.

Phinney, S.D. et al., "Human Subcutaneous Adipose Tissue Shows Site-Specific Differences in Fatty Acid Composition," Am J. Clin. Nutr., 60:725-29, 1994.

Rabi, "Metabolic adaptations in brown adipose tissue of the hamster in extreme ambient temperatures," American Journal of Physiology 231, 153-160 (1976).

Renold, A.E., "Adipose Tissue," Handbook of Physiology, Chapter 15:170-76, 1965.

Rubinsky, "Cryosurgery: advances in the application of low temperatures to medicine," Int. J. Refrig. 190-199 (1991).

Schoning, et al., "Experimental Frostbite: Freezing Times, Rewarming Times, and Lowest Temperatures of Pig Skin Exposed to Chilled Air," Cryobiology, 1990, pp. 189-193, 27.

Shephard, "Adaptation to Exercise in the Cold," Sports Medicine, 1985, 2:59-71.

Winkler et al., "Gene Transfer in Laboratory Fish: Model Organisms for the Analysis of Gene Function," Transgenic Animals, 1997, pp. 387-395.

Young, H.E. et al., "Isolation of Embryonic Chick Myosatellite and Pluripotent Stem Cells, " J. Tiss. Cult. Meth., 14:85-92, 1992.

Final Office Action; U.S. Appl. No. 10/391,221; Date of Mailing: Aug. 24, 2006, 4 pages.

Final Office Action; U.S. Appl. No. 11/016,196; Date of Mailing: Mar. 23, 2010, 12 pages.

Final Office Action; U.S. Appl. No. 11/435,502; Date of Mailing: Mar. 29, 2010, 11 pages.

International Search Report and Written Opinion for PCT/US2009/058088; Applicant: Zeltiq Aesthetics, Inc.; Date of Mailing: Nov. 20, 2009, 14 pages.

International Search Report and Written Opinion for PCT/US2009/067973; Applicant: Zeltiq Aesthetics, Inc.; Date of Mailing: Feb. 18, 2010, 10 pages.

Non-Final Office Action; U.S. Appl. No. 10/391,221; Date of Mailing: Jan. 25, 2006, 6 pages.

Non-Final Office Action; U.S. Appl. No. 10/391,221; Date of Mailing: May 30, 2007, 8 pages.

Non-Final Office Action; U.S. Appl. No. 10/391,221; Date of Mailing: Jul. 22, 2005, 6 pages.

Non-Final Office Action; U.S. Appl. No. 11/016,196; Date of Mailing: Apr. 22, 2008, 11 pages.

Non-Final Office Action; U.S. Appl. No. 11/016,196; Date of Mailing: Sep. 25, 2009, 8 pages.

Non-Final Office Action; U.S. Appl. No. 11/359,092; Date of Mailing: Nov. 19, 2009, 13 pages.

Non-Final Office Action; U.S. Appl. No. 11/528,225; Date of Mailing: Apr. 12, 2010, 11 pages.

Pre-Interview Office Action; U.S. Appl. No. 11/434,478; Date of Mailing: May 6, 2010, 4 pages.

Non-Final Office Action; U.S. Appl. No. 11/558,046; Date of Mailing: Jul. 12, 2010, 14 pages.

Non-Final Office Action; U.S. Appl. No. 11/741,271; Date of Mailing: Jul. 12, 2010, 9 pages.

European Search Report, European Patent Application No. 10167756.5, Applicant: The General Hospital Corporation, Mailing Date: Aug. 31, 2010, 6 pages.

International Search Report and Written Opinion for PCT/US2010/033290; Applicant: Zeltiq Aesthetics, Inc.; Mailed on Feb. 25, 2011, 12 pages.

International Search Report and Written Opinion for PCT/US2011/022112; Applicant: Zeltiq Aesthetics, Inc.; Mailed on Mar. 18, 2011, 11 pages.

International Search Report and Written Opinion for PCT/US2011/022444; Applicant: Zeltiq Aesthetics, Inc., Mailed on Mar. 29, 2011, 14 pages.

Merrill, Tom, "A Chill to the Heart: A System to Deliver Local Hypothermia Could One Day Improve the Lives of Heart-Attack Patients," Mechanical Engineering Magazine, Oct. 2010 (10 pages).

Non-Final Office Action; U.S. Appl. No. 12/942,852; Date of Mailing: Jun. 30, 2011, 10 pages.

Non-Final Office Action; U.S. Appl. No. 11/528,225; Date of Mailing: Aug. 3, 2011, 13 pages.

Non-Final Office Action; U.S. Appl. No. 12/565,613; Date of Mailing: Sep. 23, 2011, 55 pages.

Wang et al., "Cryopreservation of cell/hydrogel constructs based on a new cell-assembling technique", Sep. 5, 2009, 40 pages.

Wharton et al., "Cold acclimation and cryoprotectants in a freeze-tolerant Antarctic nematode, Panagrolaimus davidi," Mar. 7, 2000, 2 pages.

Zeltiq Aesthetics, Inc., Supplementary European Search Report and Search Opinion dated Jan. 12, 2012, European Paten Application No. EP08798416.7, 7 pages.

European Search Report, European Patent Application No. EP07761461; Applicant: Zeltiq Aesthetics, Inc., Mailing Date: Apr. 25, 2012, 9 pages.

European Search Report, Supplement, European Patent Application No. EP09836823, Applicant: Zeltiq Aesthetics, Inc., Mailing Date: May 15, 2012, 5 pages.

International Search Report and Written Opinion; International Application No. PCT/US2012/022585; Mailing Date May 18, 2012, 12 pages.

Non-Final Office Action; U.S. Appl. No. 11/1777,992; Mailing Date: Jun. 22, 2012, 5 pages.

Final Office Action; U.S. Appl. No. 11/750,953; Mailing Date: Jul. 5, 2012, 11 pages.

Final Office Action; U.S. Appl. No. 11/741,271; Mailing Date: Jul. 19, 2012, 8 pages.

* cited by examiner

MONITORING THE COOLING OF SUBCUTANEOUS LIPID-RICH CELLS, SUCH AS THE COOLING OF ADIPOSE TISSUE

CROSS-REFERENCE TO RELATED APPLICATION

The present application claims priority to U.S. Provisional Application Ser. No. 60/957,130, filed Aug. 21, 2007, the disclosure of which is incorporated herein by reference in its entirety.

INCORPORATION BY REFERENCE OF COMMONLY-OWNED APPLICATIONS

The following commonly-assigned U.S. patent applications are incorporated herein by reference in their entireties:

U.S. patent application Ser. No. 11/750,953, filed on May 18, 2007, (Publication No. 2008/0287839), entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2007/0198071, now U.S. Pat. No. 7,854,754, entitled "COOLING DEVICE FOR REMOVING HEAT FROM SUBCUTANEOUS LIPID-RICH CELLS"; U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. patent application Ser. No. 11/933,066, filed Oct. 31, 2007 (Publication No. 2009/0118722), entitled "METHOD AND APPARATUS FOR COOLING SUBCUTANEOUS LIPID-RICH CELLS OR TISSUE";

U.S. patent application Ser. No. 11/777,995, filed Jul. 13, 2007 (Publication No. 2009/0018624), entitled "LIMITING USE OF DISPOSABLE PATIENT PROTECTION DEVICES";

U.S. patent application Ser. No. 11/777,992, filed Jul. 13, 2007 (Publication No. 2009/0018623), entitled "SYSTEM FOR TREATING LIPID-RICH REGIONS";

U.S. patent application Ser. No. 11/777,999, filed Jul. 13, 2007 (Publication No. 2009/0018625), entitled "MANAGING SYSTEM TEMPERATURE TO REMOVE HEAT FROM LIPID-RICH REGIONS";

U.S. patent application Ser. No. 11/778,003, filed Jul. 13, 2007 (Publication No. 2009/0018627), entitled "SECURE SYSTEM FOR REMOVING HEAT FROM LIPID-RICH REGIONS";

U.S. patent application Ser. No. 11/778,001 (Publication No. 2009/0018626), entitled "USER INTERFACES FOR A SYSTEM THAT REMOVES HEAT FROM LIPID-RICH REGIONS," filed Jul. 13, 2007, and U.S. Patent Publication No. 2008/0077202, now U.S. Pat. No. 8,192,474, entitled "TISSUE TREATMENT METHODS".

TECHNICAL FIELD

The present application relates generally to treatment devices, systems, and methods for removing heat from lipid-rich cells, such as subcutaneous lipid-rich cells.

BACKGROUND

Excess body fat, or adipose tissue, may be present in various locations of the body, including, for example, the thigh, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. In contrast, methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Overview

Figure 1:
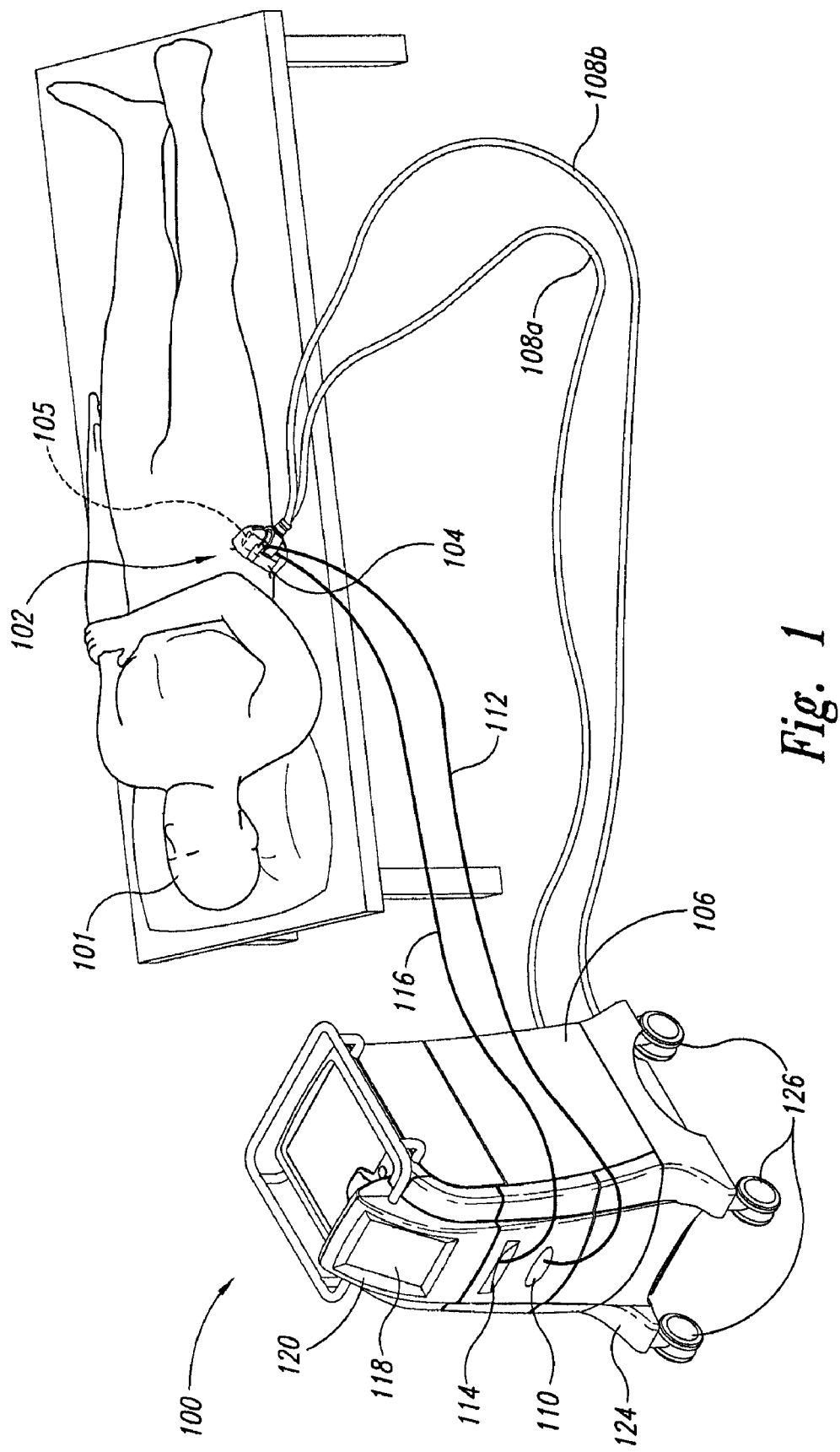
FIG. 1 is an isometric view schematically illustrating a treatment system for treating subcutaneous lipid-rich regions of a patient in accordance with an embodiment of the disclosure.

Devices, systems, and methods for monitoring and closed loop controlling of the treatment (including cooling) of subcutaneous tissue, such as adipose tissue, are described. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Systems and methods described herein are directed toward monitoring, controlling, and/or detecting treatment events associated with a treatment device used to treat subcutaneous lipid-rich cells of a subject. Specific embodiments of such systems and methods are directed toward monitoring, controlling, and/or detecting treatment events associated with a treatment device used to remove heat from subcutaneous lipid-rich cells of a subject. In some examples of the system, a treatment device applies cooling directly to a location of the skin. Without proper control or due to unanticipated circumstances, a treatment such as a cooling treatment may be less than fully successful. For example, a cooling treatment may initiate or cause freezing of the skin, the treatment device may move away from a desirable position on a patient, and/or the quality of the treatment may be lower than a specified standard or threshold. Thus, it may be desirable for subjects to receive treatment from devices and associated systems that are able to detect various events that may occur during a treatment, such as a cooling treatment, among other benefits.

In some examples, the system detects an event during a treatment such as a cooling treatment and performs one or more actions based on that detection, such as shutting off or reducing power delivered to the treatment device, otherwise enabling or initiating an alternative treatment such as warming the skin, alerting an operator of the treatment device of the event, logging data and other information about a treatment, and so on.

In some examples, the system determines the occurrence of a treatment event by detecting an increase in temperature of the skin or underlying tissue. The system may monitor the temperature of a treatment device in contact with the skin and determine the occurrence of the treatment event at the skin when the temperature of the treatment device, or a portion of the device, increases. For example, the system may determine the occurrence of a treatment event when a portion of the treatment device that directly contacts the skin increases in temperature.

The magnitude and/or the rate of the temperature increase may provide information about the type of treatment event. For example, a first range of measured temperature increases may indicate a freezing event or a partial freezing of skin, while a second such range may indicate a movement event of a treatment device.

In some examples, the system additionally may monitor the location and/or movement of the treatment device and may prevent false or inaccurate determinations of treatment events based on such monitoring. For example, the device may move during treatment, causing the device to contact a warmer area of skin, to no longer contact the skin, and so on. That is, the system may register a difference in temperature that is inconsistent with a normal treatment. The system may be configured to differentiate between this increase in temperature and a temperature increase associated with a treatment event, and, for instance, provide an indication or alarm to alert the operator to the source of this temperature increase. In the case of a temperature increase not associated with a treatment event, the system may also suppress the false indication, while in the case of a temperature increase associated with freezing, take any number of actions based on that detection as described elsewhere herein.

In some examples, the system may rely on two or more temperature measurements to more accurately determine a treatment event during a cooling treatment, such as when a device is initially cooled to a target temperature or when a device loses contact with a targeted location. In some cases, the system may identify a temperature change within a contact layer of the device, such as a portion of the device that contacts the skin. Additionally, the system may identify a temperature change within a component responsible for cooling, such as a temperature sensor in or proximate the thermoelectric cooler that cools the contact layer to a desired temperature to effect a desired cooling of tissue under the skin. The system may then determine a treatment event based on both temperature changes. The system may also use laterally spaced temperature sensors within a common layer to make a decision.

Suitable Treatment System

FIG. 1 and the following discussion provide a brief, general description of a suitable treatment system 100 in which aspects of the disclosure can be implemented. Those skilled in the relevant art will appreciate that the disclosure can be practiced with other treatment systems and treatment protocols, including invasive, minimally invasive, other non-invasive medical treatment systems, and/or combinations of one or more of the above for treating a patient. In general, the term "treatment system", as used generally herein, refers to any of the above system categories of medical treatment as well as any treatment regimes or medical device usage.

The treatment system 100 is suitable for treating a subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. When cooling subcutaneous tissues to a temperature lower than 37° C., subcutaneous lipid-rich cells can selectively be affected. In general, the epidermis and dermis of the patient 101 lack lipid-rich cells compared to the underlying lipid-rich cells forming the adipose tissue. Because non-lipid-rich cells usually can withstand colder temperatures better than lipid-rich cells, the subcutaneous lipid-rich cells can selectively be affected without affecting the non-lipid-rich cells in the dermis, epidermis and other surrounding tissue. In some embodiments, the treatment system 100 can apply cooling temperatures to the skin of the patient in a range of from about −20° C. to about 20° C. In other embodiments, the cooling temperatures can be from about −20° C. to about 10° C., from about 0° C. to about 20° C., from about −15° C. to about 5° C., from about −5° C. to about 15° C., or from about −10° C. to about 0° C.

Without being bound by theory, the selective effect of cooling on lipid-rich cells is believed to result in, for example, membrane disruption, cell shrinkage, disabling, destroying, removing, killing or other method of lipid-rich cell alteration. Such alteration is believed to stem from one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure also is believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

In various embodiments, the system 100 includes a controller, a computing device, a data acquisition device, a chiller, and one or more applicators. The system can employ these components in various embodiments to receive a selection of a treatment profile and apply the selected treatment using an applicator.

FIG. 1 is an isometric view illustrating a treatment system 100 for non-invasively removing heat from subcutaneous lipid-rich regions of a subject patient 101 in accordance with an embodiment of the disclosure. The system 100 may include a treatment device 104 including an applicator 105 that engages a target region of the subject 101. The treatment device 104 may be placed, for example, at an abdominal area 102 of the subject 101 or another suitable area for cooling or removing heat from the subcutaneous lipid-rich cells of the subject 101. It will be understood that treatment devices 104 and applicators 105 can be provided having various, configurations, shapes and sizes suitable for different body regions and body parts such that any suitable area for removing heat from a subcutaneous lipid-rich region of the subject 101 can be achieved.

An applicator, such as applicator 105, is a component of the system 100 that cools a region of a subject 101, such as a human or animal (i.e., "patient"). Various types of applicators may be applied during treatment, such as a vacuum applicator, a belt applicator (either of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators and their configurations usable with system 100 variously are described in, e.g., commonly assigned U.S. Patent Publication Nos. 2007/0198071, 2008/0077201, and 2008/0077211 and in U.S. patent application Ser. No. 11/750,953. In further embodiments, the system 100 may also include a patient protection device (not shown) incorporated into or configured for use with the applicator that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

The system 100 may further include a treatment unit 106 and supply and return fluid lines 108a-b between the treatment device 104 and the treatment unit 106. The treatment unit 106 can remove heat from a coolant to a heat sink and provide a chilled coolant to the treatment device 104 via the fluid lines 108a-b. Alternatively, chiller 106 can circulate warm coolant to the cooling device 104 during periods of warming. Examples of the circulating coolant include water, glycol, synthetic heat transfer fluid, oil, a refrigerant, and/or any other suitable heat-conducting fluid. The fluid lines 108a-b may be hoses or other conduits constructed from polyethylene, polyvinyl chloride, polyurethane, and/or other materials that can accommodate the particular circulating coolant. The treatment unit 106 may be a refrigeration unit, a cooling tower, a thermoelectric chiller or cooler, or any other device capable of removing heat from a coolant. Alternatively, a municipal water supply (i.e., tap water) may be used in place of the treatment unit. Furthermore, one skilled in the art will recognize that there are a number of other cooling technologies that could be used such that the treatment unit or chiller need not be limited to those described herein.

In this example, the treatment device 104 includes at least one applicator 105 and at least one treatment unit. The applicator 105 may provide mechanical energy to create a vibratory, massage, and/or pulsatile effect. The applicator 105 may include one or more actuators, such as, motors with eccentric weight, or other vibratory motors such as hydraulic motors, electric motors, pneumatic motors, solenoids, other mechanical motors, piezoelectric shakers, and so on, to provide vibratory energy to the treatment site. Further examples include a plurality of actuators for use in connection with a single treatment device 104 and/or applicator 105 in any desired combination. For example, an eccentric weight actuator may be associated with one treatment device 104 or applicator 105, while a pneumatic motor may be associated with another section of the same treatment device or applicator. This, for example, would give the operator of treatment system 100 options for differential treatment of lipid rich cells within a single region or among multiple regions of subject 101. The use of one or more actuators and actuator types in various combinations and configurations with a treatment device 104 or applicator 105 may be possible.

The treatment unit may be a Peltier-type thermoelectric element, and the treatment device 104 may have a plurality of individually controlled treatment units to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Cooling devices having multiple individually controlled heat exchanging units are described in commonly assigned U.S. Patent Publication No. 2008/0077211.

The system 100 may further include a power supply 110 and a processing unit 114 operatively coupled to the treatment device 104 and the applicator 105. In one example, the power supply 110 provides a direct current voltage to a thermoelectric treatment device 104 and/or the applicator 105 to remove heat from the subject 101. The processing unit 114 may monitor process parameters via sensors (not shown) placed proximate to the treatment device 104 through power line 116 to, among other things, adjust the heat removal rate based on the process parameters. The processing unit 114 may further monitor process parameters to adjust the applicator 105 based on the process parameters.

The processing unit 114 may be in direct electrical communication with treatment device 104 through electrical line 112 as shown in FIG. 1; alternatively, processing unit 114 may be connected to treatment device via a wireless or an optical communication link. Processing unit 114 may be any processor, Programmable Logic Controller, Distributed Control System, and so on. Note that power line 116 and line 112 are shown in FIG. 1 without any support structure. Alternatively, power line 116 and line 112 (and other lines including, but not limited to fluid lines 108a-b) may be bundled into or otherwise accompanied by a conduit or the like to protect such lines, enhance user safety and ergonomic comfort, ensure unwanted motion (and thus potential inefficient removal of heat from subject 101) is minimized, and to provide an aesthetic appearance to system 100. Examples of such a conduit include a flexible polymeric, fabric, or composite sheath, an adjustable arm, etc. Such a conduit (not shown) may be designed (via adjustable joints, etc.) to "set" the conduit in place for the treatment of subject 101.

In another aspect, the processing unit 114 may be in electrical or other communication with an input device (such as touch screen 118), an output device 120, and/or a control panel (not shown). The input device may be a keyboard, a mouse, a touch screen, a push button, a switch, a potentiometer, any combination thereof, and any other device or devices suitable for accepting user input. The output device 120 may include a display or touch screen, a printer, a medium reader, an audio device, any combination thereof, and any other device or devices suitable for providing user feedback. In the embodiment of FIG. 1, the output device 120 is a touch screen that functions as both an input device 118 and an output device. The control panel may include visual indicator devices or controls (lights, numerical displays, etc.) and/or audio indicator devices or controls. The control panel may be a component separate from the input device and/or output device, may be integrated with one or more of the devices, may be partially integrated with one or more of the devices, may be in another location, and so on. In alternative examples, the control panel, or parts thereof (described herein) may be contained in, attached to, or integrated with the treatment device 104 and/or applicator 105. In this example, processing unit 114, power supply 110, control panel, treatment unit 106, input device 118, and output device 120 are carried by a rack or cart 124 with wheels 126 for portability. In alternative examples, the processing unit 114 may be contained in, attached to, or integrated with the treatment device 104 and/or the applicator 105 and/or the patient protection device described above. In yet another example, the various components may be fixedly installed at a treatment site. Further details with respect to components and/or operation of treatment device 104, treatment unit 106, applicator 105 and other components may be found in commonly-assigned U.S. patent application Ser. No. 11/750,953.

Without being bound by theory, it is believed that in operation effective cooling from the treatment device, which cools through conduction, depends on a number of factors. Exemplary factors that impact heat removal from the skin area and related tissue include the surface area of the treatment unit, the temperature of the interface member and the mechanical energy delivered to the tissue. More specifically, in operation, and upon receiving input to start a treatment protocol, the processing unit 114 can cause the applicator 105 to cycle through each segment of a prescribed treatment plan. In so doing, the applicator 105 applies power to one or more treatment devices 104, such as thermoelectric coolers (e.g., TEC "zones"), to begin a cooling cycle and, for example, activate features or modes such as vibration, massage, vacuum, etc. Using temperature sensors (not shown) proximate to the one or more treatment devices 104, the patient's skin, a patient protection device, or other locations or combinations thereof, the processing unit 114 determines whether a temperature or heat flux that is sufficiently close to the target temperature or heat flux has been reached. It will be appreciated that while a region of the body (e.g., adipose tissue) has been cooled or heated to the target temperature or by a target heat flux, in actuality that region of the body may be close but not equal to the target temperature, e.g., because of the body's natural heating and cooling variations. Thus, although the system may attempt to heat or cool to the target temperature or by a target heat flux, a sensor may measure a sufficiently close temperature. If the target temperature has not been reached, power can be increased or decreased to change heat flux, as needed, to maintain the target temperature or "set-point." When the prescribed segment duration expires, the processing unit 114 may apply the temperature and duration indicated in the next treatment profile segment. In some embodiments, temperature can be controlled using a variable other than, or in addition to, power.

Although a noninvasive applicator is illustrated and discussed herein, minimally invasive applicators may also be employed. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007-0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004-0215294, entitled "CRYOTHERAPY PROBE"; U.S. Pat. No. 7,083,612, entitled "CRYOTHERAPY SYSTEM"; and U.S. Publication No. 2005-0261753, entitled "METHODS AND SYSTEMS FOR CRYOGENIC COOLING".

According to examples of the system, the applicator 105 and the treatment device 104 combine to enhance disruption of cooled adipose tissue. Further, the examples may provide reduced treatment time, reduced discomfort to the patient and increased efficacy of treatment.

Examples of the system may provide the treatment device 104 and the applicator 105 which damage, injure, disrupt or otherwise reduce subcutaneous lipid-rich cells generally without collateral damage to non-lipid-rich cells in the treatment region. In general, it is believed that lipid-rich cells selectively can be affected (e.g., damaged, injured, or disrupted) by exposing such cells to low temperatures that do not so affect non-lipid-rich cells. As a result, lipid-rich cells, such as subcutaneous adipose tissue, can be damaged while other cells in the same region are generally not damaged even though the non-lipid-rich cells at the surface are subject to even lower temperatures. The mechanical energy provided by the applicator may further enhance the effect on lipid-rich cells by mechanically disrupting the affected lipid-rich cells.

In some examples of the system, a cryoprotectant is used with the treatment device to, among other advantages, assist in preventing freezing of non lipid-rich tissue (e.g., dermal tissue) during treatment as is described in commonly-assigned U.S. Patent Publication No. 2007/0255362.

In one mode of operation, the applicator is coupled to a treatment device. The treatment device may be configured to be a handheld device such as the device disclosed in commonly-assigned U.S. patent application Ser. No. 11/359,092, filed on Feb. 22, 2006, entitled TREATMENT DEVICE FOR REMOVING HEAT FROM SUBCUTANEOUS LIPID-RICH CELLS, which is incorporated by reference in its entirety.

Applying the treatment device with pressure or with a vacuum type force to the subject's skin or pressing against the skin may be advantageous to achieve efficient treatment. In general, the subject 101 has a body temperature of about 37° C., and the blood circulation is one mechanism for maintaining a constant body temperature. As a result, blood flow through the skin and subcutaneous layer of the region to be treated may be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the treatment device with pressure, can improve the efficiency of tissue cooling and avoid excessive heat loss through the dermis and epidermis. Additionally, a vacuum may pull skin away from the body which can assist in cooling underlying tissue.

By cooling the subcutaneous tissue to a temperature lower than 37° C., subcutaneous lipid-rich cells selectively may be damaged. In general, the epidermis and dermis of the subject 101 have lower amounts of unsaturated fatty acids compared to the underlying lipid-rich cells forming the subcutaneous tissues. Because non-lipid-rich cells usually can withstand colder temperatures better than lipid-rich cells, the subcutaneous lipid-rich cells can be selectively injured while maintaining the non-lipid-rich cells in the dermis and epidermis. An exemplary range may be from about −10° C. to about 0° C.

Figure 2:
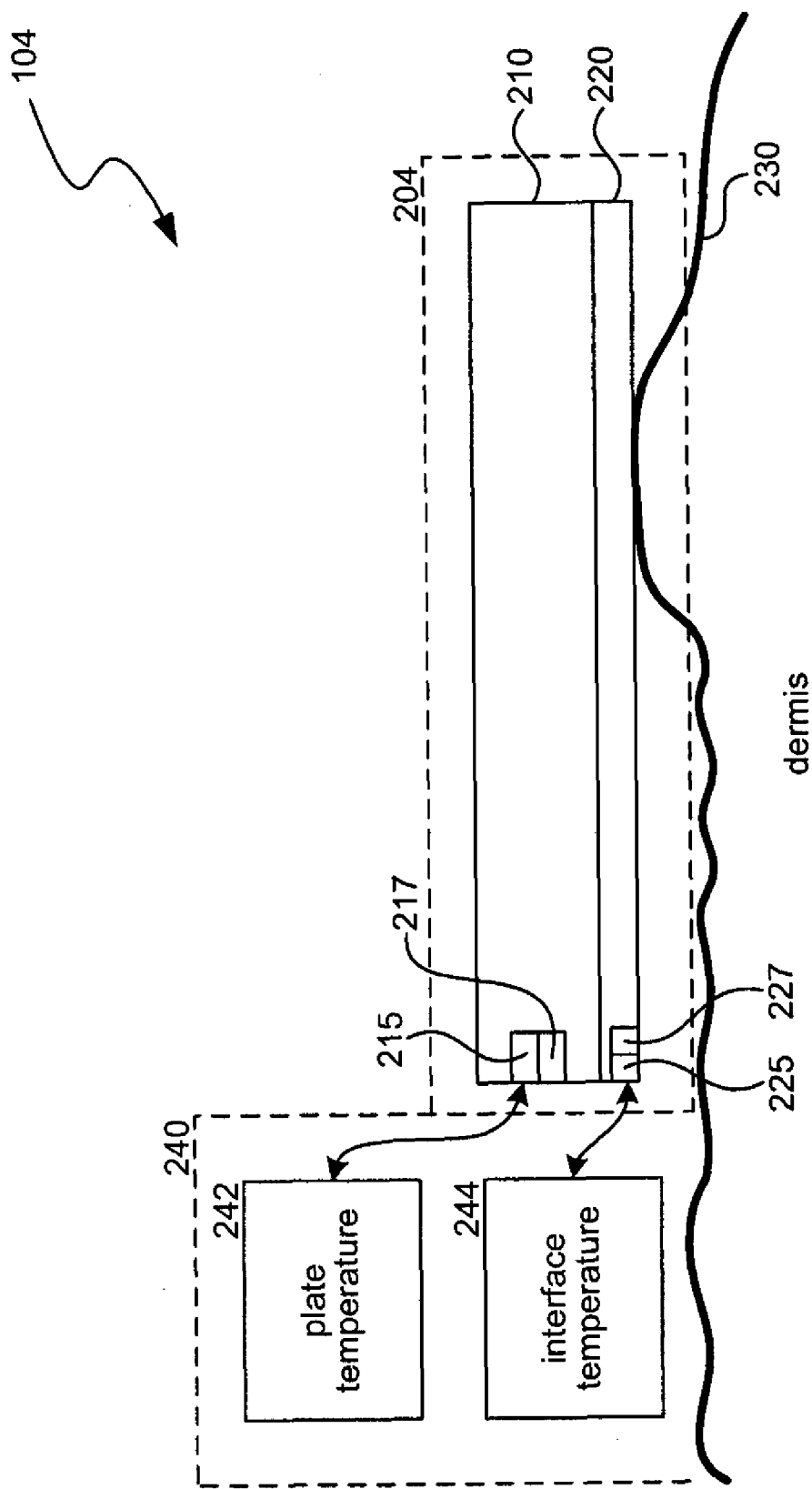
FIG. 2 is a schematic illustrating a treatment device for treating subcutaneous lipid-rich regions of a patient in accordance with an embodiment of the disclosure.

FIG. 2 is a schematic illustrating a treatment device 104 for removing heat from subcutaneous lipid-rich cells. Treatment unit 104 may include a cooling unit, such as a cooling plate 210, and an interface layer 220. Interface layer 220 may be a plate, a film, a covering, or other suitable materials described herein and may serve as the patient protection device described herein. The interface layer 220 is located between the cooling plate 210 and the skin 230 of a subject (not shown), such as the skin of a patient receiving treatment via the treatment device 104. The cooling plate 210 may contain a communication component 215 that communicates with a controlling device 240 as described herein, and a temperature measurement component 217 that measures the temperature of the cooling plate 210. The interface layer 220 may also contain a similar communication component 225 and a temperature measurement component 227 that measures the temperature of the interface layer 220. For example, communication components 215, 225, and/or both may receive and transmit information from controlling device 240, such as temperature information determined by temperature measurement units 217, 227, and/or both. The device 104 may also contain power components and other components described with respect to FIG. 1 and related applications.

In some cases, the treatment device may include a device having a sleeve and/or interface layer that is used to contact the patient's skin. For example, the treatment device may include a sleeve having a first sleeve portion and a second sleeve portion. The first sleeve portion may contact and/or facilitate the contact of the treatment device with the patient's skin. The second sleeve portion may be an isolation layer extending from the first sleeve portion. For example, the second sleeve portion may be constructed from latex, rubber, nylon, Kevlar®, or other substantially impermeable or semi-permeable material. The second sleeve portion may prevent contact between the patient's skin and the cooling plates, among other things. Further details regarding a sleeve device may be found in U.S. Patent Publication No. 2008/0077201.

In some cases, the treatment device may include a device having a belt assists in forming a contact between the treatment device (such as via an interface layer) and the patient's skin. For example, the treatment device may include retention devices coupled to a frame. The retention devices may be rotatably connected to the frame by retention device coupling elements. The retention device coupling elements, for example, may be a pin, a ball joint, a bearing, or other type of rotatable joints. Alternatively, the retention devices may be rigidly affixed to the end portions of cooling element housings. Further details regarding a belt device may be found in U.S. Patent Publication No. 2008/0077211.

In some cases, the treatment device may include a device having a vacuum that assists in forming a contact between the treatment device (such as via the interface layer) and the patient's skin. For example, the treatment device may provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. patent application Ser. No. 11/750,953.

Figure 3:
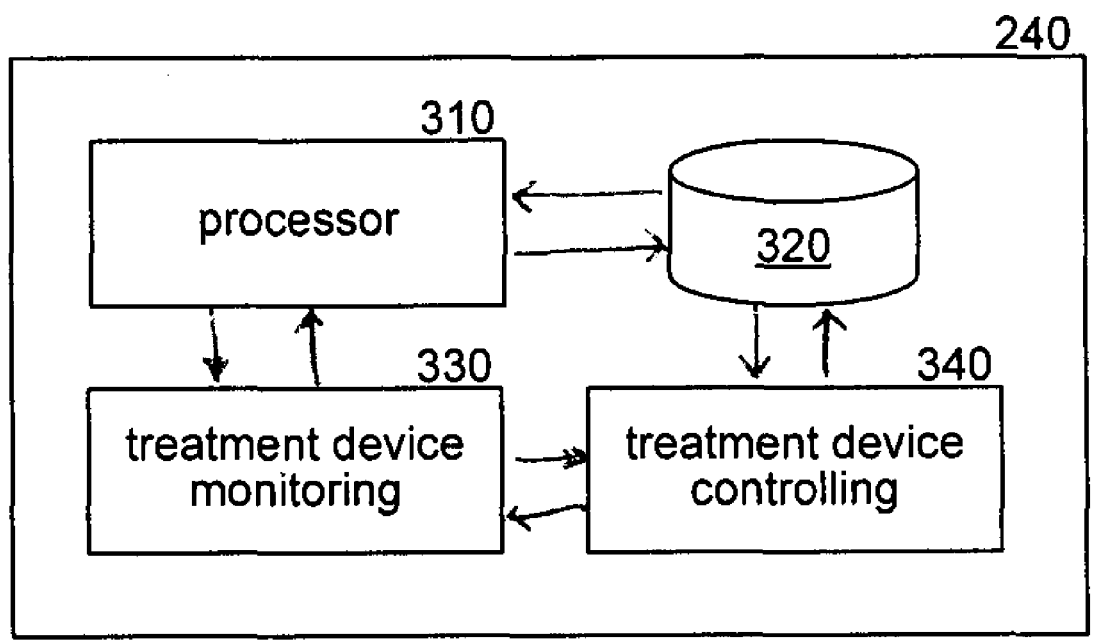
FIG. 3 is a block diagram illustrating subcomponents of a controlling device for treating subcutaneous lipid-rich regions of a patient in accordance with an embodiment of the disclosure.

FIG. 3 is a block diagram illustrating a controlling device 240 in communication with a treatment device 104 used for removing heat from subcutaneous lipid-rich cells. Controlling device 240 includes a processor 310 that may include an input component, a database component, a process component, an output component, and other components. The processor 310 may store or retrieve data and other information from database 320, such as memory or other components. The controlling device 240 also contains a treatment device monitoring component 330 and a treatment device controlling component 340. Components 330 and 340 act to monitor operation of the treatment device 104 and control the operation the treatment device 104, respectively. For example, component 330 may perform or receive temperature measurements related to components of the treatment device 104 and component 340 may operate the treatment device based on those measurements. Additionally, the component 330 may perform or receive measurements related to the movement or location of the treatment device 104, and component 340 may operate the treatment device based on those measurements. For example, during a cooling operation or other use of the treatment device 104, the monitoring component 330 may identify when a treatment event occurs or may estimate when one will occur using the system described herein. Upon receipt of such identification, the monitoring component 330 may alert the controlling component 340 which may perform an action to alter or pause the treatment. The processor 310 may facilitate data flows between the components, and may search the database 320 for information, such as information that defines treatment events, information related to the patient, and other pertinent information.

As described herein, the system may administer cooling to a patient using a number of different types of devices.
Monitoring Controlling, and Detecting Events During the Removal of Heat from Cells As described above, the system detects events during a cooling treatment, such as skin freezing during supercooling of subcutaneous tissue, skin freezing during cooling of subcutaneous tissue, movement of a treatment device to a warmer area of the skin, lifting of the treatment device off the skin, undesirable treatment quality, and so on.

In some examples the system performs closed loop control of treatment devices, such as the closed loop control of cooling using temperature components or sensors within the treatment devices. For example, as described herein, the system includes a treatment device that performs conductive cooling of subcutaneous tissue under the skin of a patient and a controlling device that controls power to the treatment device to lower the temperature of the device in order to cool the subcutaneous tissue. The system includes a component that monitors the cooling of the subcutaneous tissue and performs actions, such as actions that prevent freezing of the skin during the cooling of the subcutaneous tissue. For example, the component detects changes in temperature at an interface between the treatment device and the skin. The component may contain a routine, algorithm, executable script, or other data structure or program module capable of detecting temperature changes and performing actions based on detected temperature changes.

During the cooling or supercooling of the subcutaneous tissue, the tissue reaches a temperature below 0° C., such as temperatures between about −10° C. and about 0° C. In some cases, dermal tissue (i.e., skin) may also reach a temperature below 0° C., such as a temperature below the freezing point of biological tissue and fluids, approximately −1.8° C. In these cases, the skin being supercooled below its freezing point may quickly freeze, forming crystals and releasing energy associated with the latent heat of crystallization of the skin.

The freezing, or crystallization, of this supercooled tissue is manifested by an increase in the tissue's temperature that is attributable to the latent heat of fusion. A treatment device, such as treatment device 104, that contacts freezing or crystallized tissue may attempt to further cool the tissue, which leads to increased power being supplied to the treatment device. The system, via a monitoring component, may detect changes in the temperature of the treatment device (e.g., the device gets colder to attempt to cool the tissue warmed by crystallization during freezing) or in the power supplied to the treatment device (e.g., the device receives more power from the system to provide additional cooling). The system may also recognize the changes relate to a variation in operational procedure and perform corrective actions to remedy the variations, as described in more detail below.

Figure 4:
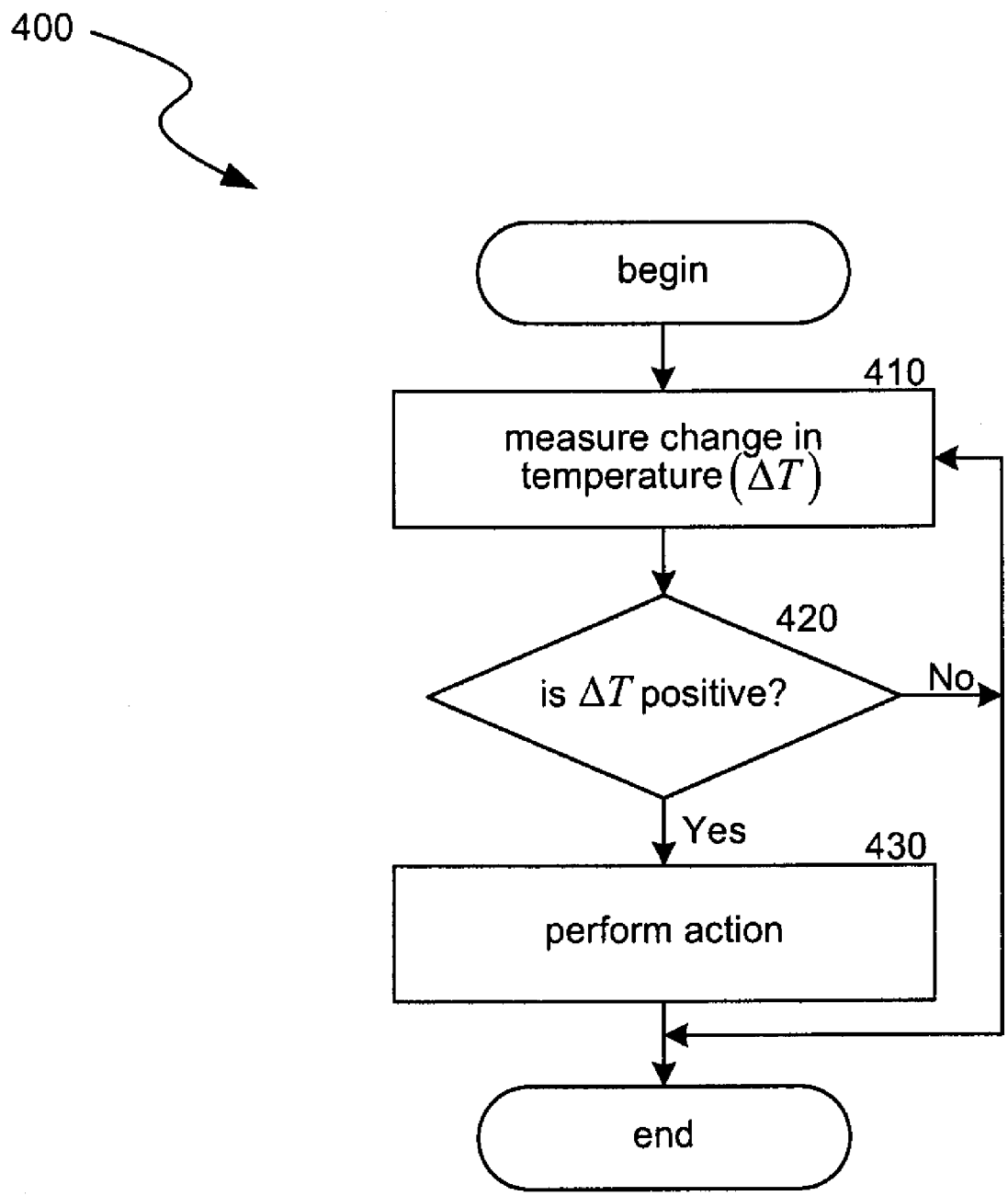
FIG. 4 is a flow diagram illustrating a routine for controlling the treatment of subcutaneous lipid-rich regions of a patient in accordance with an embodiment of the disclosure.

Referring to FIG. 4, a flow diagram illustrating a routine 400 for controlling the removal of heat from subcutaneous lipid-rich cells during a treatment event at the skin in the vicinity of the subcutaneous lipid-rich cells is shown. In step 410, the system measures changes in temperature at a location on the skin. For example, the system measures the temperature of interface layer 220 at predefined or predetermined time intervals. Alternatively, the system may continuously monitor the temperature of the interface layer 220 and/or measure the temperature at certain times and calculate the time rate of change of the temperatures.

In step 420, the system determines if the change of temperature is positive (increase) or negative (decrease). If the change of temperature is positive, routine 400 proceeds to step 430, else the routine proceeds back to step 410 and continues monitoring the device or, in some cases, ends. In some cases, the system may detect a positive change of temperature only when the change of temperature is above a threshold value for the change. For example, a small change of temperature in a positive direction may not indicate a treatment event, especially if it is then followed by a negative change or no change to the temperature. The system may, therefore, only consider changes in temperature that satisfy threshold values in magnitude and/or speed of change. Thus, in some cases the system can prevent small variations in temperature from causing false alarms with respect to false treatment events and other minimal procedural variations that do not adversely affect a procedure.

In step 430, upon detecting a positive change in temperature, the system performs an action, such as a preventative action that identifies or counteracts the treatment event. For example, the system may shut off power to the treatment device, may raise the temperature of the treatment device to warm a freezing or frozen area of skin, may alert an operator of the treatment device to remove the treatment device from the subject or perform other preventative measures, may send a message to a database that maintains operational data of the device or to a database related to the subject, and so on. Combinations of various actions, such as simultaneously alerting an operator of a detected freezing event and warming of the treatment device, for example, may also be utilized.

In some cases, routine 400 may monitor the power used by the treatment device, such as power used by a thermoelectric cooler within the device. Alternatively, routine 400 may monitor a power surrogate, such as the current, a pulse width modulation duty cycle in a controller used by the treatment device, and so on. Upon the occurrence of a treatment event at the skin and subsequent warming of the skin due to the freezing event, the supply of power to the treatment device increases. For example, in order to maintain the treatment device at a specified temperature, the system is configured to provide additional power to the thermoelectric cooler when such warming is detected. Routine 400 may detect the increase in power, such as a power spike, and perform some or all of the actions described in step 430.

Example Treatment Events

Figure 5A:
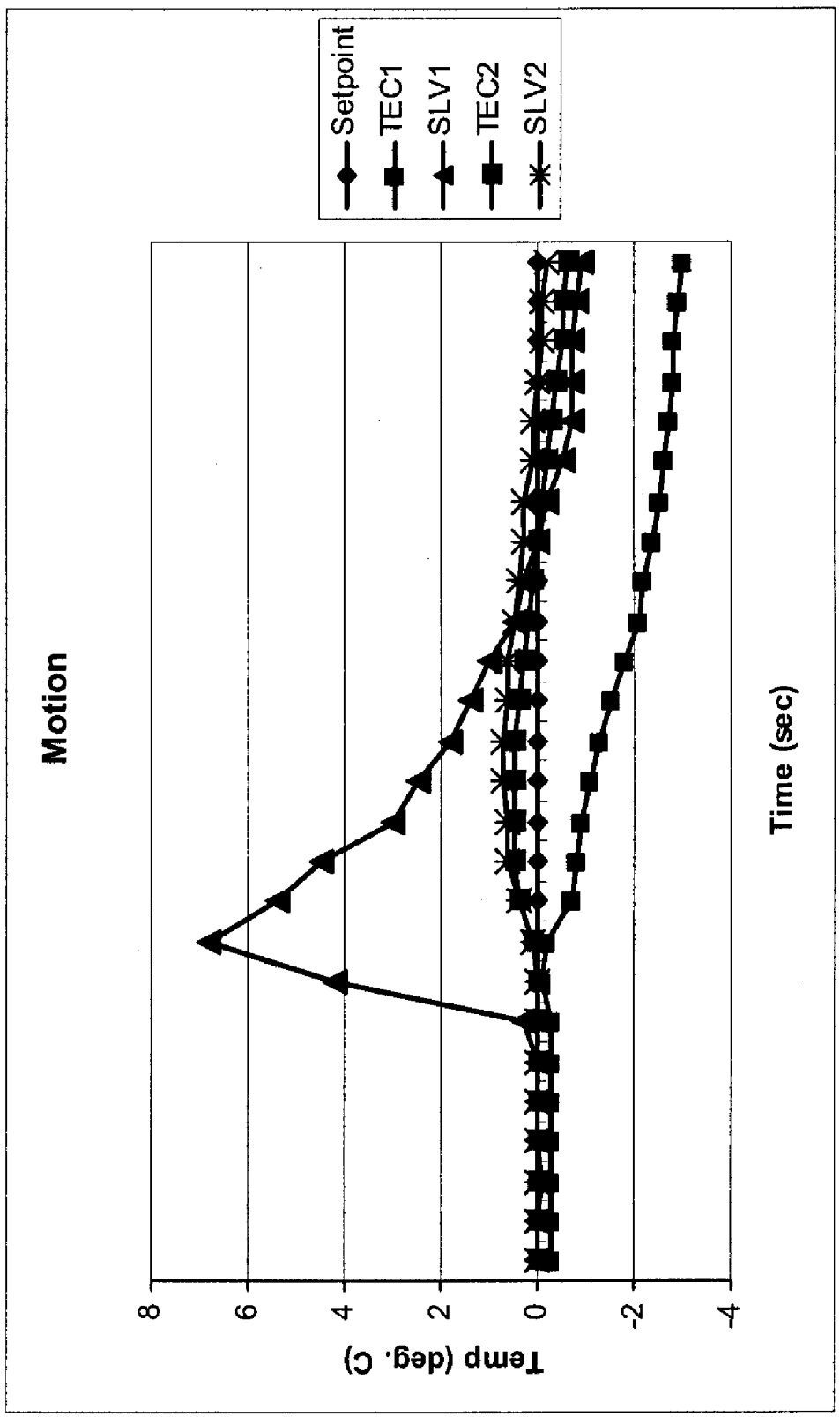
FIGS. 5A-5C are graphs illustrating the detection of treatment events of a subject during the treatment of subcutaneous lipid-rich regions of a patient.
Figure 5B:
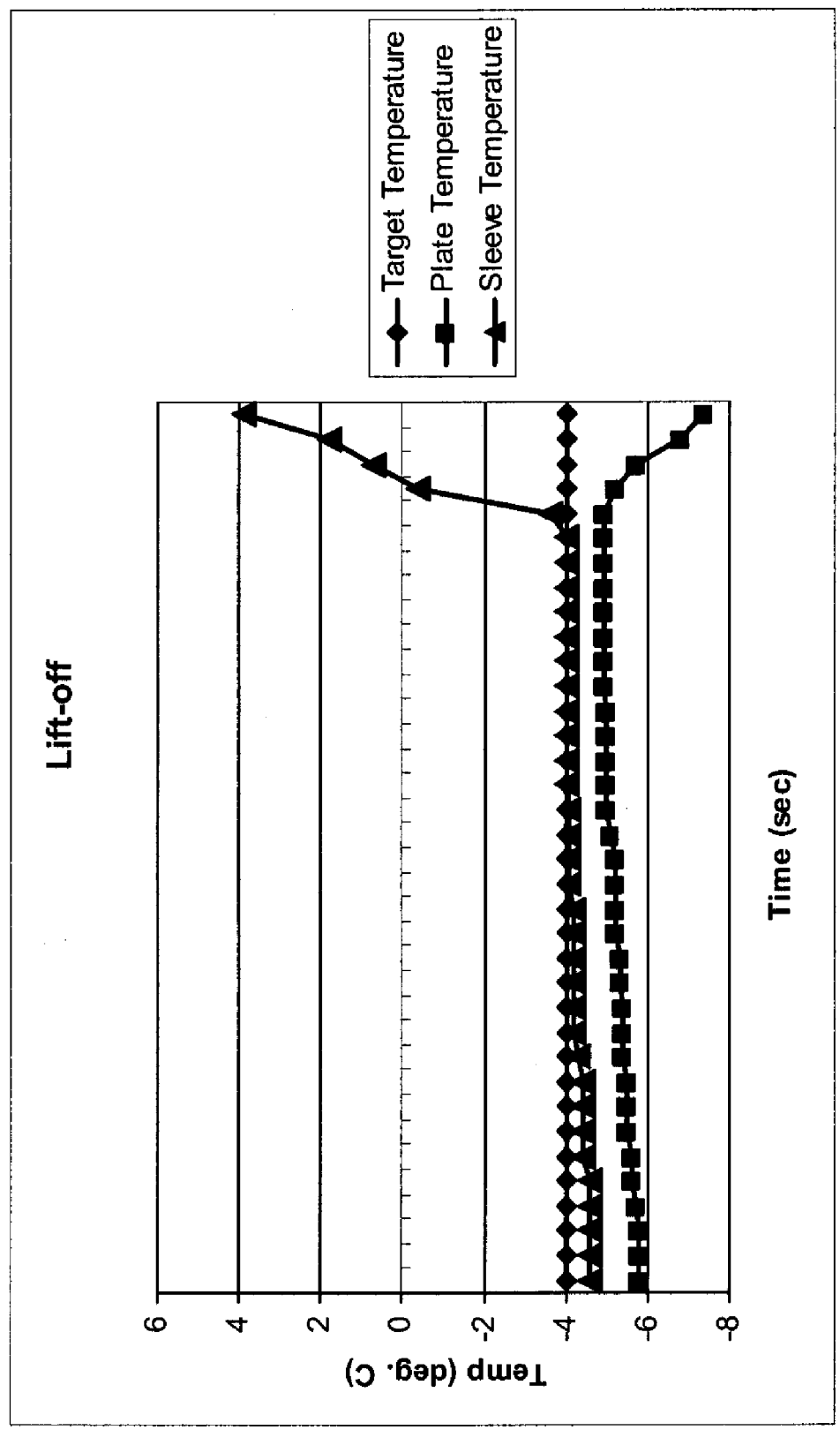
Figure 5C:
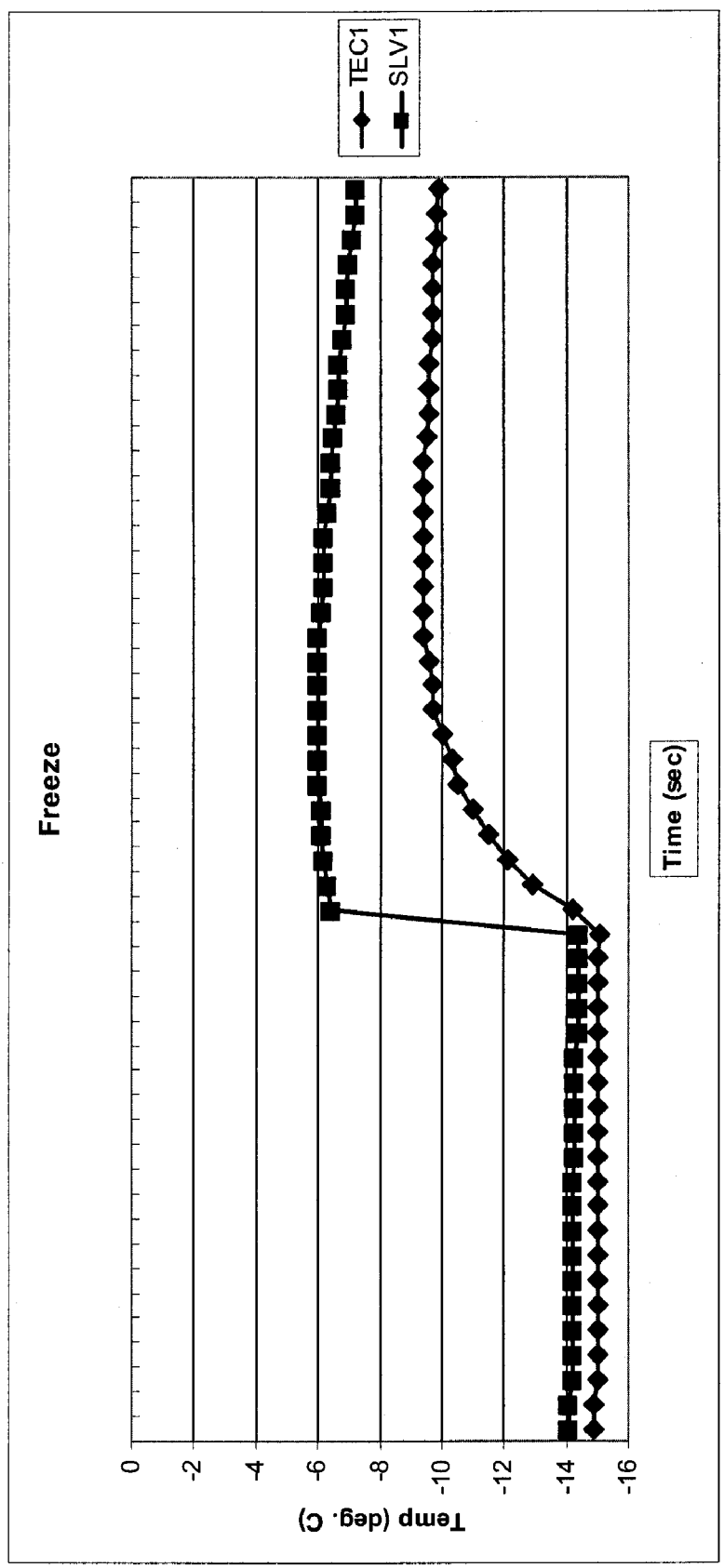

FIGS. 5A to 5C are graphs illustrating treatment events that may occur at a location on the skin of a subject during the removal of heat from subcutaneous lipid-rich cells utilizing system 100. Referring to FIG. 5A, a plot of measured treatment device temperatures (such as temperature for interface layers and cooling plates) versus time, indicating a lateral motion event during treatment, is shown. During a treatment, the temperature of the interface layer (SLV1) rises while the other temperatures minimally change. Using such feedback, the system may detect that a treatment device, such as a sleeve device, has moved away from a treatment area on a patient's skin.

Referring to FIG. 5B, a plot of measured device temperatures versus time, indicating a liftoff event, is shown. During a treatment, the sleeve temperature rises while the plate temperature decreases. Using such feedback, the system may detect that a treatment device has been lifted off, removed, separated, partially separated, or otherwise has lost contact or partially lost contact from a target location on a patient's skin.

Referring to FIG. 5C, a plot of measured device temperatures versus time, indicating a freezing event, is shown. During a treatment, the sleeve temperature (SLV1) rises while the plate temperature (TEC1) also rises, although to a smaller magnitude and with a smaller rate of change. Using such feedback, the system may detect that a freezing event has occurred on the skin of a patient.

Robust Detection of Treatment Events During a Cooling Treatment

As described herein, the system may detect a change in temperature of the treatment device, and thus possibly an anomalous event, using one or more temperature sensors. For instance, one temperature sensor may be located at or within a cooling plate 210, and a second temperature sensor may be located at or within an interface layer 220. In this example, measuring changes in temperature at both the plate 210 and the interface 220 reduces a possible erroneous detection of a freezing event due to the lifting off of the treatment device from the skin. Other configurations and locations for one or more temperature sensors and corresponding algorithms for processing the data received from each sensor relative to the detection of a skin freezing event are possible.

Figure 6:
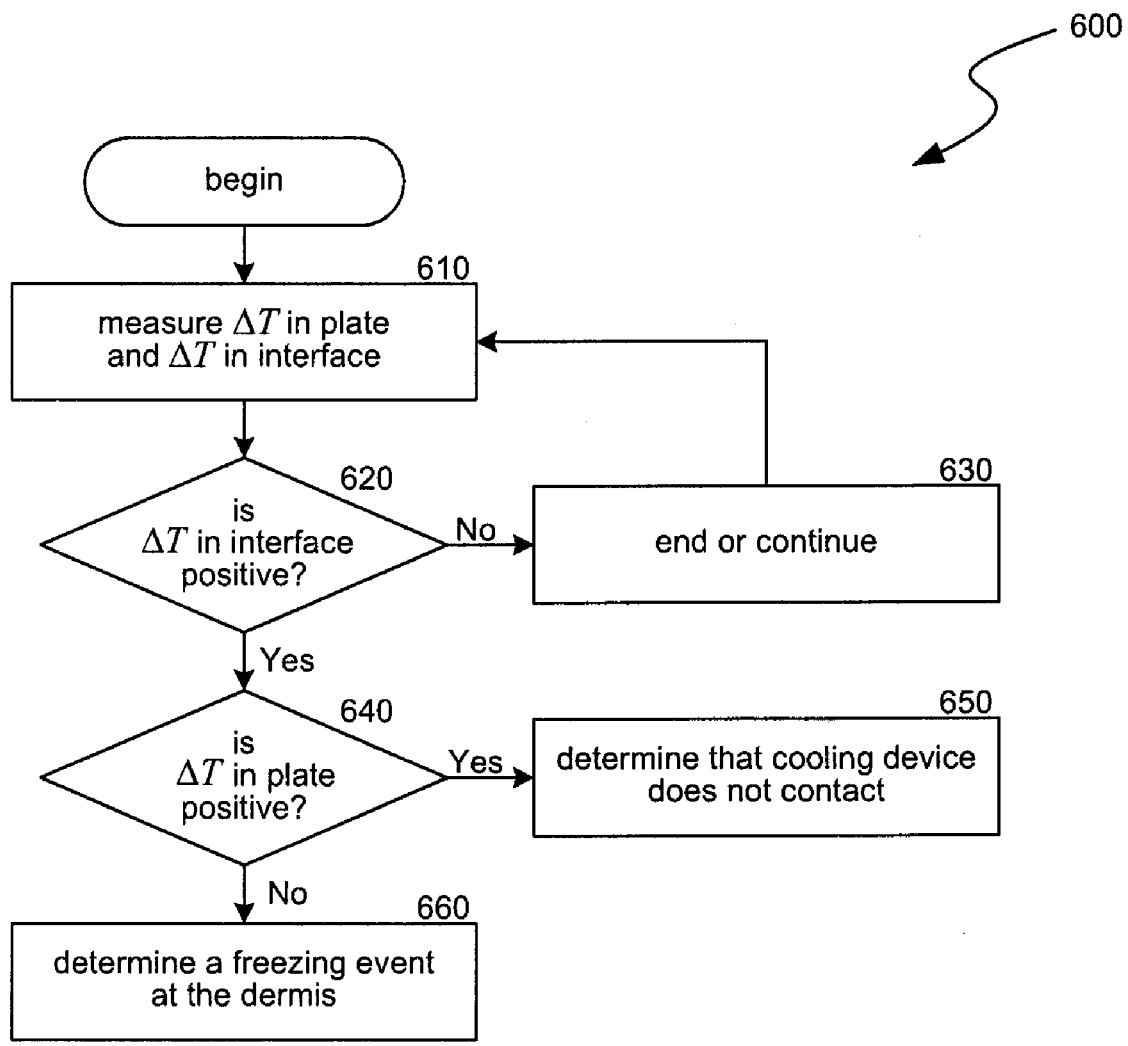
FIG. 6 is a flow diagram illustrating a routine for detecting a freezing event during the treatment of subcutaneous lipid-rich regions of a patient.

Referring to FIG. 6, a flow diagram illustrating a routine 600 for controlling the removal of heat from subcutaneous lipid-rich cells is shown utilizing a system configured with two temperature sensors, as described above. In step 610, the system measures the rate of change of the temperature of the cooling plate 210 and the rate of change of the temperature of the interface layer 220. In step 620, if the rate of change of the temperature of the interface layer 220 is positive, routine 600 proceeds to step 640, else routine 600 proceeds to step 630 and either ends or proceeds back to step 610 and continues monitoring the temperatures at the two locations.

In step 640, if the system determines the rate of change of the temperature of the cooling plate 210 is positive, routine 600 proceeds to step 660, else routine 600 proceeds to step 650 and alerts the operator of the anomaly and/or that the treatment device is not in contact with the skin, has shifted from the targeted location, and so on. In these cases, the detection of a warming interface layer 220 and a cooling or stable cooling plate 210 (due to an increase in power) may indicate a misalignment or movement of the treatment device and not a freezing event. In such a case, the treatment device may be repositioned on the targeted location of the skin for continued treatment.

In step 660, having detected a positive rate of change of the temperature of the interface layer 220 at step 620 and a positive rate of change of the temperature of the cooling plate 210 at step 640, the system determines a freezing event at the location on the skin. Thus, by measuring the rate of change of temperature of the interface and the cooling plate (such as a thermoelectric cooler), the system is able to determine the difference between a likely freezing event and movement of the treatment device.

In some examples, routine 600 may measure the power supplied to the treatment device as it relates to changes of temperature of the cooling plate 210 and/or the interface layer 220. For example, in step 640, the system may determine an increase in power and a negative rate of change of the temperature of the cooling plate 210, and proceed to step 660.

The system may increase the accuracy of detection of likely freezing events by increasing the signal-to-noise ratio of detected temperatures. In some cases, measuring the rate of change of the temperature at the interface layer 220 provides a high signal-to-noise ratio, in part due to being able to control the detection environment. For example, the system can accurately control the temperature of the interface layer leading to fewer parasitic phenomena that may introduce noise into a temperature measurement signal. Additionally, the cooler the skin, the higher the ratio, providing more accurate measurements for more severe freezing events. In some cases, the system may average the rate of change of temperature or power over time for a number of seconds in order to reduce or remove the effects of background noise. A predetermined threshold, related to the average value of the rate of change measurements, may trigger an alarm or an action to be performed in order to correct or prevent a freezing event. For example, when the treatment device reaches the threshold value, power to the device may be cut off by the controlling device.

Figure 7:
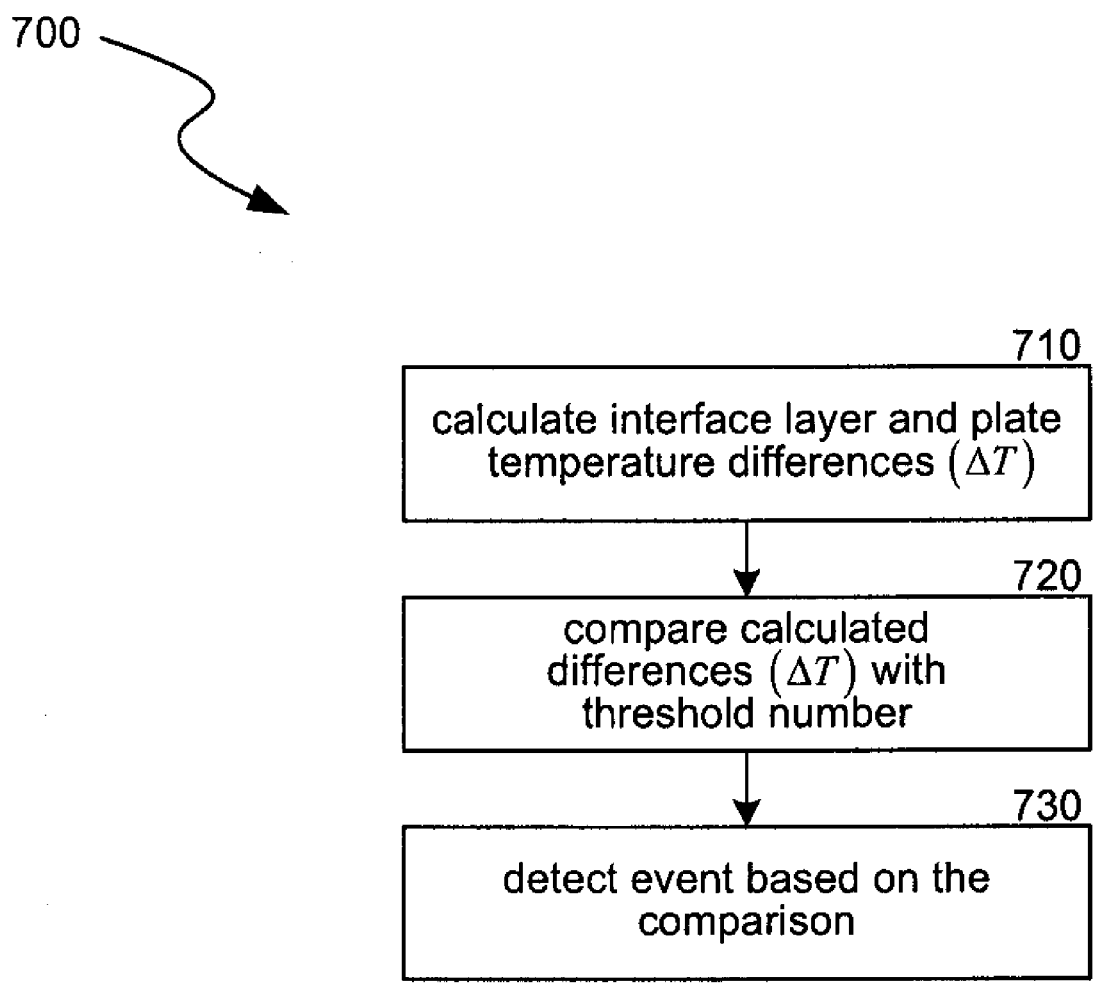
FIG. 7 is a flow diagram illustrating a routine for detecting a treatment event during the treatment of subcutaneous lipid-rich regions of a patient.

As described herein, the system may also determine the range of temperature changes during a cooling treatment, detect a treatment event based on a determined range, and perform an action appropriate for and associated with the detected event. Referring to FIG. 7, a flow diagram illustrating a routine 700 for detecting a treatment event is shown.

In step 710, the system calculates interface layer (e.g., sleeve) temperature differences and the plate temperature differences for a treatment device in use during a cooling treatment. That is, the system calculates changes of temperature for the sleeve and cooling plates of a treatment device. The system may perform a set of calculations, such as three calculations, or more, or less. In step 720, the system compares the calculated temperature differences with threshold values. For example, the system may use 4 degrees Celsius as a threshold value for a sleeve temperature difference, and 1 degree Celsius as a threshold value for a plate temperature difference. In step 730, the system detects a treatment event based on the comparison. The treatment event may be a freezing event, a liftoff event, or a motion event.

The following examples illustrate how various events may be detected during cooling treatments using routine 700.

During a first treatment, the system detects temperature differences for the sleeve above a threshold value of 4 degrees C., and detects temperature differences for the plate above 1 degree C. but below 2 degrees C. Using the detected temperatures, the system determines that a freezing event occurs.

During a second treatment, the system detects temperature differences for the sleeve above a threshold value of 4 degrees C., and detects temperature differences for the plate below 2 degrees C. Using the detected temperatures, the system determines that a liftoff event occurs.

During a third treatment, the system detects temperature differences for the sleeve to be between 1 and 5 degrees C., and performs appropriate actions. For different temperature differences, the system performs an action associated with that temperature difference. For example, for all temperature differences between 1 and 3 degrees C., the system updates a treatment log of information. However, in this example, for temperature differences above 3 degrees C., the system shuts down the treatment device.

Of course, the system may detect events based on other threshold ranges and/or values. For example, the system may perform one or more rules based algorithms, comparisons, or processes in order to detect an event based on measured changes in temperature.

Detection of Movement to Prevent Inaccurate Detections of Treatment Events

In some examples, the treatment device 104 contains location detection or other movement-based sensors, either with or without temperature sensors. At times, the treatment device deliberately or inadvertently may move during treatment. Such movement may trigger a similar temperature response as is caused by a treatment event. Thus, the system may contain components that detect movement of the device and indicate the movement to a controlling component, thus preventing a premature termination of a treatment due to a false alarm. Examples of sensor types that may be used to detect movement include accelerometers, optical sensors, and so forth.

In some examples, the system may contain a plurality of sensors, located at a central area of a treatment device and at the edges of the treatment device used to detect undesirable movement of the treatment device 104. Thus, sensor arrays may facilitate the prevention of unwanted terminations of treatment due to movement of the device 104 relative to the skin 230.

Other Detection of Treatment Events

In some examples, the system may detect a treatment event using measured characteristics affected by temperature changes. For example, during cooling of the treatment device to a desired temperature, the power may initially increase and then decrease as the temperature approaches the desired temperature, and remain approximately consistent at the desired temperature.

For example, the system measures the time rate of change of temperature of the treatment device, such as the time rate of change of the temperature of the interface layer, and measures the time rate of change of the power supplied to the device 104. Upon measuring an increase in the power supplied to the device and an increase in the temperature, the system determines a treatment event at the skin of a subject. Thus, an increase in the time rate of change of the temperature of the treatment device 104 along with an increase in the change of power indicates a likely treatment event during an initial cooling period of the treatment device 104.

In some cases, a treatment event may occur during the initial cooling period, which may be hard to detect because the temperature of a treatment device and power level of a treatment device may be rapidly changing (relative to changes seen during freezing events). Thus, in some cases the system may ramp down to an intermediate temperature (where no freezing of tissue occurs, e.g., 0 degrees C.) at a rapid pace and then slowly ramp down to the target temperature. In these cases, any jumps in power levels or spikes in temperature due to freezing events or other variations are more discernable because power and temperature are not also rapidly changing to provide cooling.

Conclusion

Systems and methods described herein monitor and control the application of cooling to subcutaneous tissue of a patient. The system detects treatment events, such as a freezing of the skin of the patient, and performs actions associated with the detected events.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The various examples described above can be combined to provide further examples. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the technology may be modified, if necessary, to employ treatment devices with a plurality of treatment units, thermally conductive devices with various configurations, and concepts of the various patents, applications, and publications to provide yet further examples of the technology.

These and other changes can be made to the technology in light of the above-detailed description. In general, in the following claims, the terms used should not be construed to limit the technology to the specific examples disclosed in the specification and the claims, but should be construed to include all cooling that operates in accordance with the claims. Accordingly, the technology is not limited by the disclosure, but instead its scope is to be determined entirely by the following claims.

We claim:

1. A non-invasive treatment system for transdermally removing heat from subcutaneous lipid-rich cells of a subject, the treatment system comprising:
   a treatment device configured to contact an area of skin of a patient and remove heat from subcutaneous lipid-rich cells located below the contacted area of skin;
   a sensor that measures a temperature of at least one of the treatment device and at least a portion of the contacted area of skin; and
   a controlling device that modifies operation of the treatment device upon determining at least a partial freezing of skin, wherein determining the at least partial freezing of skin is based upon receiving an indication from the sensor of a positive change in temperature of at least one of the treatment device and the at least a portion of the contacted area of skin.

2. The treatment system of claim 1, wherein the treatment device comprises:
   a cooling unit that removes the heat; and
   an interface layer configured to be disposed at least partially between the cooling unit and the contacted area of skin;
   wherein the controlling device further determines the at least partial freezing of skin upon detecting an increase in temperature of at least a portion of the interface layer.

3. The treatment system of claim 1, wherein the treatment device comprises:
   an plate configured to be cooled to a temperature below 0° C.;
   an interface layer that partially surrounds the plate and that is configured to contact the area of skin;
   wherein the controlling device determines at least a partial freezing of the skin upon detecting an increase in temperature of at least a portion of the interface layer.

4. The treatment system of claim 1, wherein the controlling device is configured to compare the measured temperature with a threshold value.

5. A non-invasive treatment system for transdermally removing heat from subcutaneous lipid-rich cells of a subject, the treatment system comprising:
   a treatment device configured to contact an area of skin of a patient and remove heat from subcutaneous lipid-rich cells located below the contacted area of skin, wherein the treatment device includes—
      a cooling unit that removes the heat; and
      an interface layer configured to be located at least partially between the cooling unit and the skin;
   a sensor that measures a temperature of at least one of the treatment device and at least a portion of the contacted area of skin; and
   a controlling device that modifies operation of the treatment device upon determining at least a partial freezing of skin, wherein determining the at least partial freezing of skin is based upon receiving an indication from the sensor of a positive change in temperature of at least one of the following: the treatment device, the at least a portion of the contacted area of skin, at least a portion of the interface layer, and at least a portion of the cooling unit.

6. A non-invasive treatment system for transdermally removing heat from subcutaneous lipid-rich cells of a subject, the treatment system comprising:
   a treatment device, configured to contact an area of skin of a patient and remove heat from subcutaneous lipid-rich cells located below the contacted area of skin, wherein the treatment device includes—
      a plate configured to be cooled to a temperature below 0° C.; and
      an interface layer that partially surrounds the plate and that is configured to contacts the area of skin;
   a sensor that measures a temperature of at least one of the treatment device and at least a portion of the contacted area of skin; and
   a controlling device that modifies operation of the treatment device upon determining at least a partial freezing of skin, wherein determining the at least partial freezing of skin is based upon receiving an indication from the sensor of a positive change in temperature of the at least one of the following: the treatment device, at least a portion of the contacted area of skin, at least a portion of the interface layer, and at least a portion of the plate.

* * * * *